US009183352B2

United States Patent
Berdyshev et al.

(10) Patent No.: US 9,183,352 B2
(45) Date of Patent: *Nov. 10, 2015

(54) METHOD AND ARRANGEMENT FOR PREDICTING AT LEAST ONE SYSTEM EVENT, CORRESPONDING COMPUTER PROGRAM, AND CORRESPONDING COMPUTER-READABLE STORAGE MEDIUM

(75) Inventors: Sergey Berdyshev, Baiersdorf (DE); Manuel Ebert, Baiersdorf (DE); Thomas Kraemer, Nuremberg (DE); Wolfgang Meyer, Erlangen (DE)

(73) Assignee: BIOTRONIK CRM Patent AG, Baar (CH)

( * ) Notice: Subject to any disclaimer, the term of this patent is extended or adjusted under 35 U.S.C. 154(b) by 771 days.

This patent is subject to a terminal disclaimer.

(21) Appl. No.: 12/756,549

(22) Filed: Apr. 8, 2010

(65) Prior Publication Data
US 2010/0262978 A1 Oct. 14, 2010

Related U.S. Application Data

(60) Provisional application No. 61/232,012, filed on Aug. 7, 2009.

(30) Foreign Application Priority Data

Apr. 9, 2009 (DE) .................. 10 2009 002 307

(51) Int. Cl.
| | | |
|---|---|---|
| G06F 17/00 | (2006.01) |
| G06N 5/00 | (2006.01) |
| G06F 19/00 | (2011.01) |
| G06N 5/02 | (2006.01) |
| G06N 99/00 | (2010.01) |

(52) U.S. Cl.
CPC .......... G06F 19/345 (2013.01); G06F 19/3418 (2013.01); G06N 5/025 (2013.01); G06N 99/005 (2013.01)

(58) Field of Classification Search
USPC ........................................... 706/45
See application file for complete search history.

(56) References Cited

U.S. PATENT DOCUMENTS

| | | | |
|---|---|---|---|
| 2001/0007948 A1* | 7/2001 | Stoop et al. ..................... 607/14 |
| 2002/0091972 A1* | 7/2002 | Harris et al. .................... 714/47 |
| 2002/0196149 A1* | 12/2002 | Halleck et al. ............. 340/573.1 |
| 2006/0252976 A1* | 11/2006 | Rosero ............................. 600/2 |

OTHER PUBLICATIONS

Lin, Jessica, Eamonn Keogh and Stefano Lonardi. "Visualizing and Discovering non-trivial patterns in large time series databases" Information Visualization 4, 2005. [Online] Downloaded Aug. 7, 2012 http://www.geogra.uah.es/patxi/Lin05_time_series_viz.pdf.*

(Continued)

*Primary Examiner* — Ben Rifkin
(74) *Attorney, Agent, or Firm* — Buchanan Ingersoll & Rooney PC

(57) ABSTRACT

A method, a system and an arrangement for predicting at least one system event and a corresponding computer program and a corresponding computer-readable storage medium are configured so that it is possible to predict a system event based on trends in observables over a certain period of time prior to the event occurring. One example of a system event is the failure of a system because the abnormal behavior of a component is reflected in irregularities in one or a plurality of observables. Another example of a system event is the early recognition or pre-acute prediction of a specific critical condition of a patient.

18 Claims, 3 Drawing Sheets

(56) References Cited

OTHER PUBLICATIONS

Hulten, Geoff, Laurie Spencer and Pedro DOmingos. "Mining Time-Changing Data Streams" ACM 2001 [Online] Downloaded Jan. 6, 2014 http://delivery.acm.org/10.1145/510000/502529/p97-hulten. pdf?ip=151.207.250.61&id=502529&acc=ACTIVE%20SERVICE&key=986B26D8D17D60C8AAC6AC1B60173C4E&CFID=396364977&CFTOKEN=13293013&__acm__=1389044035__2fadb4c6d93b0785714354e44801.*

* cited by examiner

Days prior to the event

METHOD AND ARRANGEMENT FOR PREDICTING AT LEAST ONE SYSTEM EVENT, CORRESPONDING COMPUTER PROGRAM, AND CORRESPONDING COMPUTER-READABLE STORAGE MEDIUM

CROSS-REFERENCE TO RELATED APPLICATIONS

This application claims the priority of German Patent Application No. DE 10 2009 002 307.0, filed on Apr. 9, 2009 in the German Patent Office and U.S. Provisional Patent Application No. 61/232,012, filed on Aug. 7, 2009 in the U.S. Patent Office, the disclosures of which are incorporated herein in their entirety by reference.

FIELD OF THE INVENTION

The invention is related to predicting system events in complex systems.

BACKGROUND OF THE INVENTION

In complex processes or systems, events are triggered by a number of factors. These factors can have a heterogeneous appearance so that even different behaviors by factors can lead to the same event. Predicting events, such as for instance a so-called decompensation event in cardiac patients, has therefore been very imprecise in the past.

It is therefore the object of the present invention to provide a method and an arrangement for predicting at least one system event and a corresponding computer program and a corresponding computer-readable storage medium for predicting an event that avoid the aforesaid disadvantages and in particular are robust with respect to heterogeneity of signal progressions prior to specific events.

SUMMARY OF THE INVENTION

In accordance with the invention, this object is attained using the features in the independent claim(s). The dependent claims identify more detailed additional useful embodiments of the invention. The subject-matter of the invention is a method, system and an arrangement for predicting at least one system event and is a corresponding computer program and a corresponding computer-readable storage medium. Embodiments of the method, system and arrangement permit it to be possible to predict the event based on trends in observables over a certain period of time prior to the event occurring. The method can be used with linear and non-linear progressions and with leaps in the observables. An event can be, for example, the failure of a system because the abnormal behavior of a component is reflected in irregularities in one or a plurality of observables or can be the early recognition or pre-acute prediction of a specific critical condition of a patient. The systems or arrangements that utilize an embodiment of the method may be applied in a variety of systems, such as economic or business systems. Embodiments of the system may be used in making decisions to take actions that adjust to the predicted event, such as selling stock, providing preventive care, or maintaining equipment. Such actions may permit an early action on a problem and resolve an issue for a much lower cost or may permit the early action to be much more effective or much more likely to be effective relative to taking similar actions after the predicted event actually occurs.

In accordance with the invention, embodiments of the arrangement, system and method may be configured so that prediction of events is based on one or more fundamental assumptions such as the assumption that system changes are reflected in changes in the signal progressions and that under stable conditions the signal progression of the system does not exhibit systematic changes apart from random fluctuations.

The signal progression of a system prior to an event to be detected is divided into individual segments of a given length, so-called windows of observation. These segments are tested for a certain form of variability in that the hypothesis that trends are present in the various segments is tested. The frequency of the trends for a defined quantity of these windows is determined. This variable is calculated for all measured variables. Then a suitable combination of partial results for the measured variables is performed and features are constructed. The classification method is either optimized using data having known properties or applied to unknown data and the result of the method is evaluated using a machine or manual decision limit.

The result is used to derive various approaches such as, for example, triggering an alarm that indicates the malfunction of a system, signals deviations from normal behavior, initiates automated maintenance or substitution processes, notifies the physician or patient of a deterioration in the patient's condition, initiates a supporting therapy (e.g. a shock, etc.), changes the pacing scheme (stimulation scheme), or permits initiation of similar immediate measures in order to prevent damage to the system, system failure, or death of the patient.

The invention provides a method for predicting system events in the future. Predictions are made using primary parameters that were measured in a limited period of time prior to the prediction time, features that reflect the change in the system being created from the primary parameters that characterize the system during a specific range of time. The prediction period can be limited as to when it starts and ends and does not necessarily have to begin at the prediction time.

To this end, at least one time window having the length L is considered within the observation period. Within the time window, measured values $s_j$ for at least one primary parameter $S_j$ are determined. The measured values at the measurement points for the primary parameters prior to the prediction time are used in chronological sequence, and it is not necessary for there to be a valid measured value at each measurement point in the time span according to the expression $L^{max}+H^{max}-H^{min}L^{max}-H^{min}$. $L^{max}$ is the longest observed window length, $H^{max}$ and $H^{min}$ are the earliest prediction time and the latest prediction time, respectively.

For at least part of the time window, the frequency τ of each trend is determined for at least a part of the at least one primary parameter $S_j$. Preferably decreasing and/or increasing trends are observed. In one preferred embodiment, the frequencies of the decreasing and/or increasing trends for a window are calculated according to the equation $$\tau^{\pm} = \frac{1}{H_{max} - H_{min}} \sum_{j=L}^{L+H_{max}-H_{min}} \theta(\pm C(j) - K_{j,p_0}),$$

where θ(x) is the step function and $C(j)=C(L)|_{L=j}$ is determined according to $$C = \sum_{k=1}^{n-1} \sum_{l=k+1}^{n} \text{sign}(y_l - y_k) \quad (1)$$

where $$\text{sign}(y_l - y_k) = \begin{cases} 1, & y_l - y_k > 0 \\ 0, & y_l - y_k = 0 \\ -1, & y_l - y_k < 0 \end{cases}$$

is the signum function.

It has proved advantageous when at least some of the time windows are divided into a plurality of intervals and the frequency $\tau_i$ of the trend within the intervals is determined for at least one primary parameter $S_j$. Preferably the windows are divided into intervals as a function of a primary parameter $S_j$.

Moreover, it has also proved advantageous when the means for frequencies $\tau$ and/or $\tau_i$ are found for a number of windows. In one preferred embodiment, the frequencies $\tau^-$ and $\tau^+$ for each measured variable $S_j$ and each L within the intervals $[L_i^{min}, L_i^{max}]$ are measured and their means are found. The means are designated $\hat{T}^{\pm}$ and are calculated as $$\hat{T}_i^{\pm}(S_j) = \frac{1}{n_i^L} \sum_{L=L_i^{min}}^{L_i^{max}} \tau_L^{\pm}, \, i = 1, \ldots, N^L,$$

where $S_j$ is the measured signal no. j and $L_i^{min}$ and $L_i^{max}$ are the starting point and ending point, respectively, of the intervals having the length $n_i^L$ from the total quantity of intervals $N^L$.

In another preferred embodiment, it is provided that groups of primary parameters $S_j$ are formed, and the mean for frequencies $\tau$ and/or $\tau_i$ for a number of windows are found for at least one group q. It has proved advantageous when the features formed from the primary parameters are combined in a plurality of groups q according to the equation $$T_k^{\pm} = \frac{\frac{1}{n_i^q} \sum_{j=1}^{n_i^q} \beta_j \hat{T}_j^+(S_j)}{\sum_{j=1}^{n_i^q} \beta_j}, \, k = 1, \ldots, N^q.$$

$N^q$ is the number of groups, each group q combining a number of $n_i^q$ measured variables (where i=1, ..., $N^q$) and a group q also comprising only one $\hat{T}_i^{\pm}$ and the measured variables being determined, weighted by relevance, using the weighting factors $\beta_j$. The mean values $T_k^{\pm}$ are so-called features and are thus suitable as input values for classification method $C(T_k^{\pm})$. $T_k^+$ and $T_k^-$, which belong to the same group, can also be included in one classification method as combined variable $T_k$. In one preferred embodiment of the invention, it is provided that the features are determined individually for an observation object. Using such a suitable classification method provides an indicator that can be employed to suggest the occurrence (or absence) of an event. Such an indicator then indicates an imminent event. Such an event can be for instance a critical system event. Such critical events can be for instance arrhythmias, pulmonary embolisms, strokes, myocardial infarcts, angina pectoris, syncope, transitory ischemic attacks, and/or acute peripheral arteriosclerotic vascular diseases.

In accordance with the invention, it is therefore provided that a system event is signaled and/or one or a plurality of system event-related measures are initiated based on the frequency τ of a trend. This signaling can be attained for instance in that the frequencies τ and/or $\tau_i$ that are averaged, are evaluated in a classification method and the at least one system event is predicted using the classification. As stated, the mean value $T_k^{\pm}$ for instance that was calculated based on the frequency τ of a trend can advantageously be included in a classification method. Such measures can be for instance system-stabilizing measures, system-stabilizing measures including changes in medication and/or other therapeutic support measures, and automated maintenance and/or substitution processes.

One preferred embodiment provides that the classification methods are optimized using classified event data and/or control data. It has also proved advantageous when precise or imprecise classification limits are used.

Another preferred embodiment provides that determining the trend includes testing a hypothesis for the presence of the trend. Preferably the aforesaid variable C is compared to the p quantile $K_{n,p}$ of Kendall K statistics in order to determine the occurrence of a negative or positive trend with the probability $p \geq p_0$.

The measured values (=measured signals) $s_j$ of the at least one primary parameter $S_j$ are preferably measured at specific intervals of time. The time interval units can be seconds, minutes, hours, days, weeks, months, or years, and the time intervals can be different for the different primary parameters.

It should be understood that heterogeneous signal progressions can be evaluated with embodiments of the invention. The signal progressions can be linear, non-linear, or non-constant.

Another advantage embodiments of the invention may provide is that the method is robust with respect to data gaps.

The following are examples of primary parameters, but are not the only primary parameters:

all primary parameters that include the pulse rate of the patient, such as e.g. the pulse rate over a pre-defined period of time, the pulse rate during a defined resting phase, the variability of the pulse rate, and the like;

all primary parameters that determine impedances in the patient, whether using intracardial (bipolar and multipolar), intrathoracic measurements or measuring with external sensors;

all primary parameters that measure the activity of a patient in some way. All primary parameters that include the portion of left-ventricular or right-ventricular stimulated, perceived, or other events;

all primary parameters that record implant-dependent signals;

all primary parameters that measure extrasystoles regardless of their location of origin;

all primary parameters that determine the hemodynamics of a patient or other elasticities, pressures, volumes, or distances;

all primary parameters that are measured outside of an implant, such as variables that are obtained using wireless sensors or variables from devices that record data outside of the body and transmit these data telemetrically to the evaluation unit;

all biomedical primary parameters such as stimulation thresholds, electrode configurations, sensor amplifications, and offset values;

all primary parameters such as blood glucose level, other biomarkers, and similar variables;

all primary parameters that measure biometric information about the patient. All primary parameters that record additional information about a medication;

all primary parameters that are measured from electrophysiological or biochemical methods;

all primary parameters that measure signals from imaging, acoustic, or mechanical methods;

all of the aforesaid primary parameters that were first standardized and/or scaled; and all possible combinations of a plurality of the aforesaid primary parameters.

One arrangement in accordance with the invention has at least one chip and/or processor and is configured so that it is possible to execute a method for predicting at least one system event, measured values $s_j$ of at least one primary parameter $S_j$ being determined within at least one time window having the length L, the frequency $\tau$ of a trend being measured for at least a portion of the at least one primary parameter $S_j$ for at least a part of the time window, and a system event being signaled and/or system event-related measures being initiated based on the frequency $\tau$ of a trend. It should be understood that the chip and/or processor may include memory coupled to the chip and/or processor that has coding or software stored thereon for executing the method.

A computer program for predicting system events makes it possible for a data processing device, after the program has been loaded into the memory of the data processing device, to execute a method for predicting at least one system event, measured values $s_j$ of at least one primary parameter $S_j$ being determined within at least one time window having the length L, the frequency $\tau$ of a trend being measured for at least a portion of the at least one primary parameter $S_j$ for at least a part of the time window, and a system event being signaled and/or system event-related measures being initiated based on the frequency $\tau$ of a trend.

In another preferred embodiment of the invention it is provided that the inventive computer program is constructed modularly, individual modules being installed on different data processing devices.

Advantageous embodiments provide additional computer programs that can be used for executing additional method steps or method sequences specified in the description.

Such computer programs can be for instance downloadable in a data or communications network (for a fee or free of charge, freely accessible or password-protected). The computer programs provided in this manner can then be rendered useable using a method in which in accordance with some embodiments of the invention, a computer program from an electronic data network, for instance the Internet, is downloaded to a data processing device connected to the data network.

In order to perform the inventive method for predicting system events, it is provided that a computer-readable storage medium is employed on which a program is stored that makes it possible for a data processing device, after the program has been loaded into the memory of the data processing device, to execute a method for predicting at least one system event, measured values $s_j$ of at least one primary parameter $S_j$ being determined within at least one time window having the length L, the frequency $\tau$ of a trend being measured for at least a portion of the at least one primary parameter $S_j$ for at least a part of the time window, and a system event being signaled and/or system event-related measures being initiated based on the frequency $\tau$ of a trend. It should be appreciated that one example of a data processing device is a computer device for running a computer program.

More detailed aspects of advantageous embodiments of the invention are explained in the following.

Basic Calculation (Feature Structure):

In the first step, the incoming measurement signals $s_j$ of the measured variable $S_j$ undergo filtering. The measured variable $S_j$ where $j=1, \ldots, N^S$ is input in the following into the feature structure as a so-called primary parameter. The number of primary parameters is $N^S$ (superscripted symbols and numerals are indices provided there is no indication to the contrary). The first step, inter alia, checks whether the values of the measured variables are in a valid range of values.

The time series for the measured signals depends on two parameters whose significance is indicated in FIG. 1. Variable L$\epsilon$N represents an observation window between $L_{min}\epsilon$N and $L_{max}\epsilon$N the variability of a measured signal is tested in its progression. The variable H$\epsilon$N describes the lead time between the time of the prediction and the occurrence of the predicted event, which may be e.g. the time until the actual or suspected occurrence of the imminent decompensation process and runs from $H_{min}\epsilon$N to $H_{max}\epsilon$N. The window should then be checked for validity using a suitable criterion. One possibility would be a requirement that at least 50% of the measured signal values are valid.

The Mann test for trend is used for valid windows. The value $$C = \sum_{k=1}^{n-1} \sum_{l=k+1}^{n} \text{sign}(y_l - y_k) \qquad (1)$$

is calculated for each window, where $$\text{sign}(y_l - y_k) = \begin{cases} 1, & y_l - y_k > 0 \\ 0, & y_l - y_k = 0 \\ -1, & y_l - y_k < 0 \end{cases}$$

is the signum function.

The hypothesis of a negative trend is confirmed if $$C < -K_{n,p},$$

the hypothesis of a positive trend is confirmed if $$C > K_{n,p}.$$

$K_{n,p}$ is the p quantile of the Kendall K statistics. The trend result is calculated individually for each parameter tuple (L, H).

The variable L can also be divided into a quantity of $N^L$ not necessarily disjunctive intervals having the length $n_i^L$, where $i=1, \ldots, N^L$. $L_i^{min}\epsilon$N and $L_i^{max}\epsilon$N are the starting and ending points, respectively, of these intervals having the $n_i^L$. One $N^L$ and one $n_i^L$ belongs to each $S_j$ (an additional index j is only mentioned for simplification where it is absolutely necessary).

Then the mean is found for the frequencies $\tau^-$ and $\tau^+$ of the occurrence of a negative or positive trend with the probability $p \geq p_0$ for a window L over all H between $H_{min}$ and $H_{max}$, that is, from L to $L+H_{max}-H_{min}$. $p_0$ must be pre-defined corresponding to the desired reliability of the entire method. $\tau^\pm$ is thus calculated as $$\tau^\pm = \frac{1}{H^{max} - H^{min}} \sum_{j=L}^{L+H^{max}-H^{min}} \theta(\pm C(j) - K_{j,p_0}), \quad (2)$$

where $$\theta(x) = \begin{cases} 0, & x < 0 \\ 1, & x \geq 0 \end{cases}$$

is the theta function.

The frequencies $\tau^-$ and $\tau^+$ are measured and their mean is found for each measured variable $S_j$ and each L within the intervals $[L_i^{min}, L_i^{max}]$. The mean values are designated $\hat{T}^\pm$ and are calculated as $$\hat{T}_i^\pm(S_j) = \frac{1}{n_i^L} \sum_{L=L_i^{min}}^{L_i^{max}} \tau_L^\pm, \, i = 1, \ldots, N^L. \quad (3)$$

FIG. 2 provides a schematic depiction of how these mean values are found.

In another step, a plurality of measured variables are combined to create a group q so that there are $N^q$ groups, each group q combining $n_i^q$ measured variables (where $i=1, \ldots, N^q$) and a group q also comprising only one $S_j$. The frequencies $\hat{T}_i^\pm$ are found for each measured variable within a group q, with the weighting factors $\beta_j$ averaged by weight according to relevance. These mean values are $T_k^\pm$ and are calculated as $$T_k^\pm = \frac{\frac{1}{n_k^q}\sum_{j=1}^{n_k^q} \beta_j \hat{T}_j^\pm(S_j)}{\sum_{j=1}^{n_k^q} \beta_j}, \, k = 1, \ldots, N^q. \quad (4)$$

It is required that $L_i^{min}(S_i) = L_j^{min}(S_j)$, or $L_i^{max}(S_i) = L_j^{max}(S_j)$ is true for all measured signals in the sum. In Equation (4) the arithmetic mean is used for averaging the location parameter. At this point another location parameter, such as e.g. the median, can also reasonably be employed.

The result is a diagnostic feature collection having the value $$2\sum_{j=1}^{N^q} N_j^L.$$

Summation follows from the fact that $N^L$ can be different for each group q.

The mean values $T_k^\pm$ are so-called features and are thus suitable for input values for classification methods $C(T_k^\pm)$. $T_k^+$ and $T_k^-$ belonging to the same group can also be included in a classification method as combined value $T_k$.

Optimizing Process:

In order to be able to allocate the collection of features to the occurrence of events it is necessary to employ a classification method $\Delta C$ that must itself be adapted. This optimization requires classified event data over a period of $L^{max} + H^{max}$ for each primary parameter employed immediately prior to the assured event and e.g. corresponding control data sets of the same length without an event. Using data sets with assured events and in some circumstances a careful selection of control data may be required for the highest possible quality of the separation method.

Now the feature $T^\pm$ is determined for each of the parameter groups q. Such classified features are suitable for automated learning depending on the number of event and control data sets. Methods such as artificial neuronal networks, support vector machines, and the like have proved themselves in this regard. Due to the great number of sets of free parameters during the training process, a great number of classified features are needed during the training process.

If these features are not present with the frequency required for this method, a classification method should be used in which the number of free parameters is compatible with the number of available training data sets. One such possibility is presented as an example in the following:

First a feature vector is formed from the features obtained $$\vec{T} = (T_{1,1}^-, T_{1,1}^+, \ldots, T_{N^q,N^L}^-, T_{N^q,N^L}^+)$$

and it is then multiplied in a scalar manner by a classification vector $$\vec{\alpha} = (\alpha_{1,1}^-, \alpha_{1,1}^+, \ldots, \alpha_{N^q,N^L}^-, \alpha_{N^q,N^L}^+,$$

The product of this scalar multiplication is a measure for the occurrence of an event. During the training process, the initial value for event and control data is set to a fixed value $c_{Event}^{Train}$ or $c_{Control}^{Train}$ that is above or below the training threshold $c_{o,Train}$. A $c_{o,Class}$ must be found in the subsequent testing method so that the method attains a pre-defined specificity and/or sensitivity, together with the trend probability $p_o$ selected earlier in the foregoing. Discrete values (e.g., −1, 0, +1 or a finer grid) can be pre-defined for the components of the classification vector $\vec{\alpha}$ in order to further limit the degree of freedom. A maximum distance between $c_{event}$ and $c_{control}$ can also be attained by systematically varying the components of $\vec{\alpha}$. The classification function employed in this example has the form $$\Delta_{example} = \sum_{j=1}^{N^L} \left[ \sum_{k=1}^{N^q} (\alpha_{k,j}^- T_{k,j}^- + \alpha_{k,j}^+ T_{k,j}^+) \right]$$

In this example there is generally no limitation to a scalar threshold so that a hyperplane in $R^n$ should be used for the decision limit.

Applying the Method:

After optimization, the classification method can be employed for predicting an event for the time span $H^{min}$ to $H^{max}$ in the future from the perspective of time of prediction. The only requirement is $$L^{max} + H^{max} - H^{min} \quad (5)$$

measured values. The features $T_k^\pm$ obtained from this can serve as input for a selected classification method C. A system can be monitored only for a predetermined duration of time, the method may be re-started each time a new measured value occurs or at greater intervals in order to provide a prediction given standard deviations in the system. If the threshold value $c_{o,Class}$ that is determined with the optimizing method is exceeded or is not met, pre-defined measures are initiated, such as e.g. a therapeutic chain of actions.

Invalid and/or Missing Measured Values:

Prior to producing the features, the measured values for the measured variables that are used for feature calculation are subjected to a validity test. Individual measured values can either be missing because they are somehow lost within the transfer segment or after a validity test they can be marked as invalid or because they are outside of a pre-defined range of values. Examples of how embodiments of the method can manage invalid and missing measured values may include:

In the Mann test for trend in accordance with Equation (1), such measured values are ignored in that in this case the effective window length is reduced by the number of these measured values. This reduction in the window length must also then be taken into account in Equation (2).

Void and/or invalid measured values are replaced with corresponding values from an interpolation method.

Another option for managing missing values is used.

BRIEF DESCRIPTION OF THE DRAWINGS

In the following the invention is explained in greater detail using an exemplary embodiment with the enclosed drawings.

DETAILED DESCRIPTION OF THE INVENTION

Figure 1:
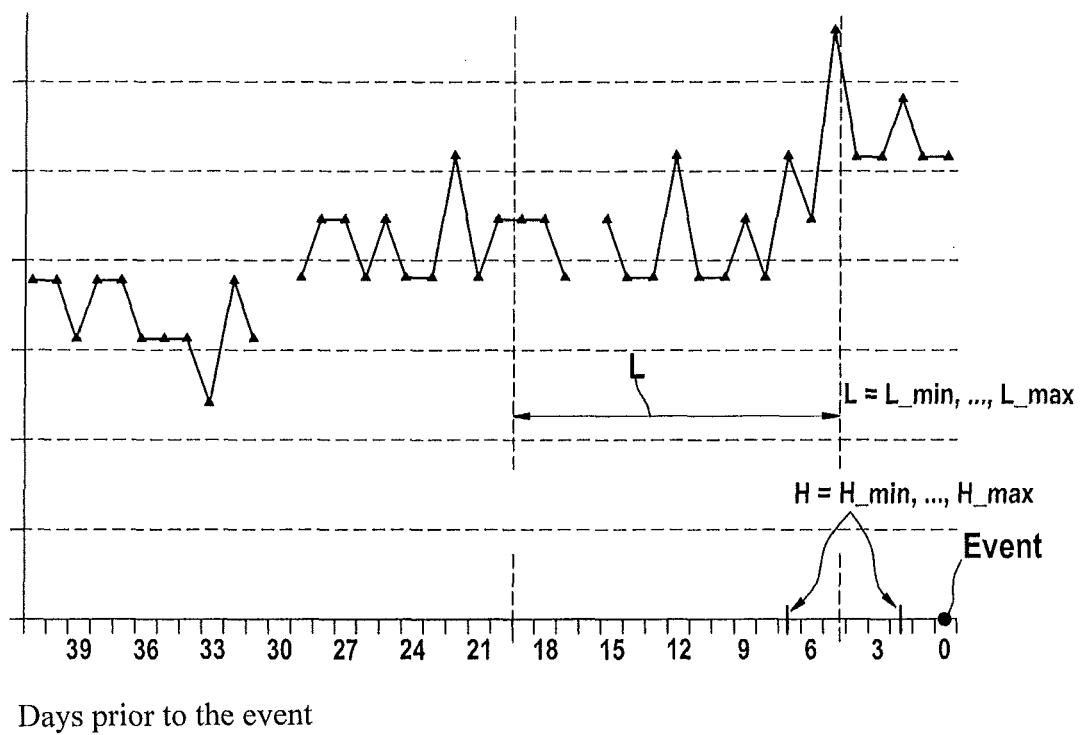
FIG. 1 is a description of the parameters $L_{min}$, $L_{max}$, $H_{min}$ and $H_{max}$.
Figure 2:
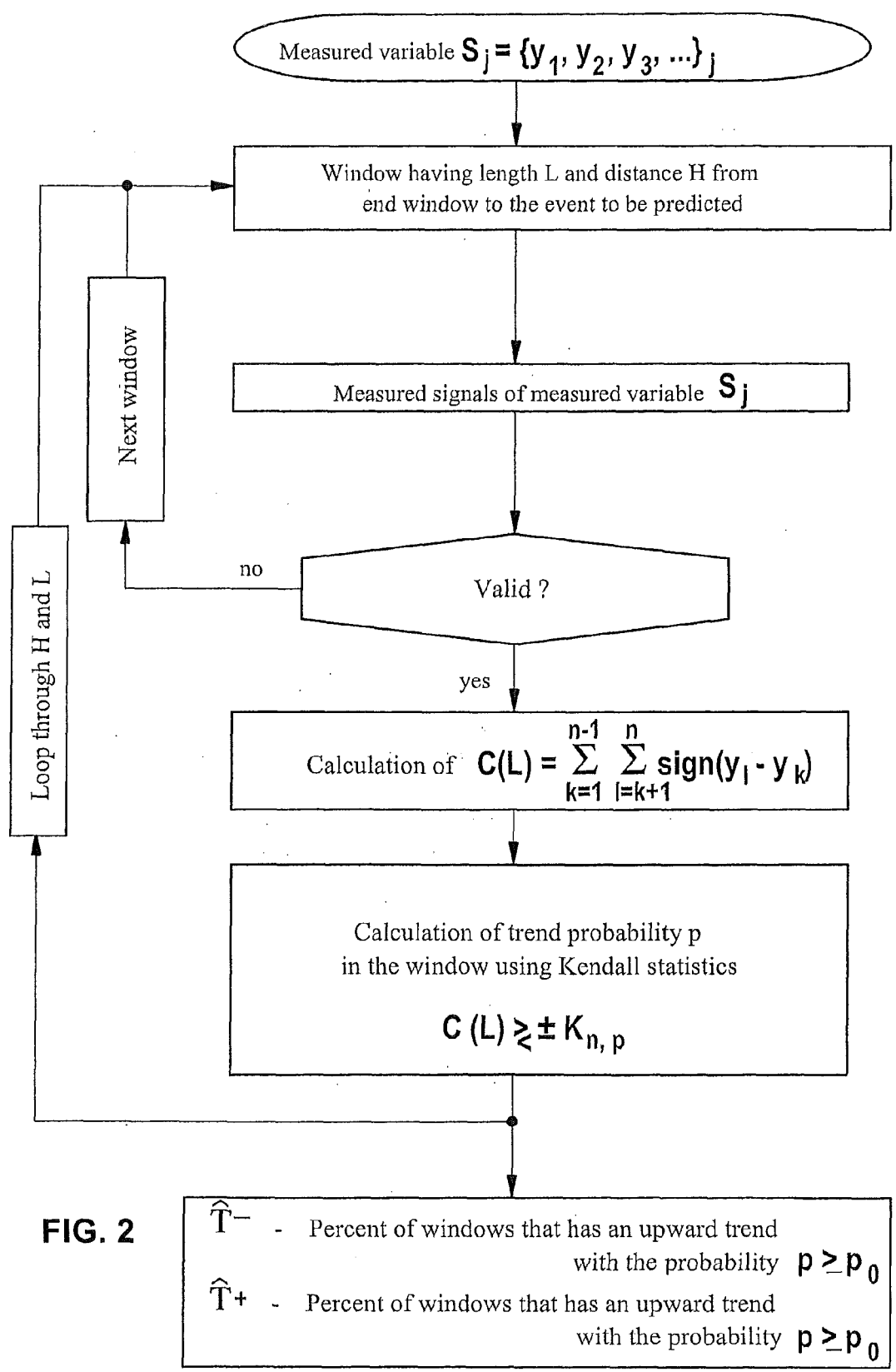
FIG. 2 is a flowchart depicting how measured data are added until the summed trend frequencies are determined.

The exemplary embodiment is a device for predicting a so-called decompensation even in patients who suffer from chronic or congestive heart failure (CHF). The invention is not limited to the medical field, however. On the contrary, it can also be used for events in other complex systems, such as for instance meteorological or geophysical systems or even economic and business systems.

It is characteristic of these patients that despite the disease being generally chronic, there are phases of an acute and brief life-threatening condition that require hospitalization. Since hospitalization is associated with high costs and the occurrence of a decompensation event is associated with high mortality and morbidity, efforts are made to use early therapeutic intervention to avoid these phases. Early detection of a potential decompensation event is required for this.

Implantation of an electrically active implant is indicated for a number of CHF patients. This is generally a CRT pacemaker (CRT=Cardiac Resynchronization Therapy) for directly addressing the reasons the heart is not pumping well by restoring synchronization of the chambers of the heart. To safeguard against sudden cardiac death, an automatic defibrillator can be implanted when there is myocardial insufficiency. With the appropriate technical equipment it is possible to determine various measured variables of a physiological or technical nature using probes and sensors in these implants. These measured variables can be processed either directly in the implant or e.g. in an external computing system in that the measured variables are transmitted from the implant to the treating physician via a patient device. Other implants or external types of devices can also be used for this.

Since some CHF patients thus currently have an electrically active implant (CRT pacemaker, ICD=Implantable Cardioverter Defibrillator), it is possible to attempt early detection of a CHF decompensation event using a home monitoring device. The systems engineering for this does not necessarily involve implants.

Depending on design, the sensors include electrodes for obtaining the intracardial electrogram, for determining impedances, pressure, and other measured variables. The measured variables themselves can undergo optional intermediate processing or can be supplied directly to an analysis unit for diagnosing a patient. However, obtaining firm diagnostic information suffers from a number of problems.

The basic disease, CHF, describes a complex pathophysiological process with a number of causes. Different types of CHF may be, for example, ischemic, non-ischemic, dilative, toxic, and idiopathic CHF. Factors such as e.g. faulty patient compliance in taking medications or adhering to a diet, acute respiratory diseases, infections, and other co-morbidities further complicate describing this underlying disease.

Due to the complexity of the underlying disease and the progression of a decompensation event, measured patient signals are heterogeneous prior to the occurrence of the events to be observed. This means different signal progressions are to be expected in different patients, and likewise the progression of two different decompensation events in one and the same patient will be different. In addition, in both cases there may be gaps in the series of measurements. The reasons for this can be losses on the telemetry segment or measured values being discarded after a validity test.

The heterogeneity in the signal progression prior to events extends to a number of different aspects:

First, differences occur in which measured variables reflect changes. For instance, it may be that initial indications of a decompensation event are first found in the level of the mean pulse rate, and changes in impedance do not occur until the actual decompensation event, but the reverse may also occur.

Secondly, the patient's reaction to an incipient decompensation event is to a certain degree behavior-dependent. This means that individual measured variables increase in one group of patients, while in another group of patients they drop, if e.g. the first group is more active because of nervousness but anxiety causes the other group to behave with more restraint.

Thirdly, the progression of the course of the disease prior to decompensation will generally differ in terms of chronological progression, which is a function of the individual constitution, behavior, and other factors. In particular other unknown, unmeasurable, uncontrollable, and individual factors may occur in the population of CHF patients.

It may be necessary to provide continuous monitoring where possible to perform measurements at least once a day. In addition, stress on the patient and costs are to be avoided, both of which could occur if false alarms occur too frequently and the patient is consequently contacted and/or hospitalized too frequently or even superfluous diagnostic and/or inadequate therapeutic intervention is undertaken. The methods must therefore also have a high degree of specificity, i.e. they must have a very low false alarm rate and therefore provide reliable support for the physician's decision-making. In addition, it should be possible to detect decompensation, with great sensitivity, for the broadest possible group of patients.

In order to ensure sufficient statistical quality it is therefore necessary to use a method that is robust with respect to the aforesaid heterogeneities. Added to this is the nature of the disease, such that a specific progression pattern for a decompensation event for each patient may not be known a priori.

It can be assumed that:

pathophysiological changes in the cardiovascular substrate must be reflected in signal changes compared to the normal status; and given stable physiological conditions, the observable measured variables must not have any systematic changes apart from random fluctuations.

These two assumptions represent the essential foundation that is the basis for the variant of a suitable algorithm that is described in this section.

Management of the method shall be the focus in the following, using a sample selection of parameter values.

Observation window: $L_{min}=8$, $L_{max}=28$

Lead time for prediction: $H_{min}=2$, $H_{max}=12$

Number of primary parameters: $N^S=8$

Required trend probability: $p_o=0.99$

Number of intervals: $N^L=N_j^L=3$ for each primary parameter $S_j$ $S_j$

Starting point and end point for the intervals:
$L_1^{min}=8$, $L_1^{max}=14$, $L_2^{max}=21$, $L_3^{min}=22$, $L_3^{max}=28$ Length of the intervals: $n_{1,j}^L = n_{2,j}^L = n_{3,j}^L = 7$ for each primary parameter $S_j$ Number of primary parameter groups: $N^q=4$ Number of primary parameters per group: $n_1^q=3$, $n_2^q=1$, $n_3^q=3$, $n_4^q=1$ Weighting factors: $\beta_1=\beta_2=\beta_3=\beta_4=1$ Size of collection of diagnostic features: $2\Sigma_{j=1}^{N^q} N_j^L = 24$ $2\Sigma_{j=1}^{N^q} N_j^L = 24$ The primary parameters can be selected from the following group:

All measured variables that include the pulse rate of the patient, such as e.g. the pulse rate over a pre-defined period of time, the pulse rate during a defined resting phase, the variability of the pulse rate, and the like;

All variables that determine impedances in the patient, whether using intracardial (bipolar and multipolar), intrathoracic measurements or measuring with external sensors;

All measured variables that measure the activity of a patient in some way;

All measured variables that include the portion of left-ventricular or right-ventricular stimulated, perceived, or other events;

All measured variables that record implant-dependent signals;

All measured variables that measure the extrasystoles, regardless of their location of origin;

All measured variables that determine the hemodynamics of a patient or other elasticities, pressures, volumes, or distances;

All measured variables that are measured outside of an implant, such as variables that are obtained using wireless sensors or variables from devices that record data outside of the body and transmit these data telemetrically to the evaluation unit;

All biomedical measured values such as stimulation thresholds, electrode configurations, sensor amplifications, and offset values;

All measured values such as blood glucose level, other biomarkers, and similar variables;

All measured values that measure biometric information about the patient;

All measured values that record additional information about a medication;

All measured values that are measured from electrophysiological or biochemical methods;

All measured values that measure signals from imaging, acoustic, or mechanical methods;

All of the aforesaid measured values that were first standardized and/or scaled; and Possible combinations of a plurality of the aforesaid measured values.

The aforesaid parameter values may yield the following classification function:

$$\Delta_{example} = \sum_{j=1}^{3}\left[\sum_{k=1}^{4}(\alpha_{k,j}^{-}T_{k,j}^{-} + \alpha_{k,j}^{+}T_{k,j}^{+})\right]$$

where $$T_{1,j}^{\pm} = \frac{1}{7}\sum_{L=L_j^{min}}^{L_j^{max}}\frac{1}{3}(\hat{T}_{Par1}^{\pm}(L) + \hat{T}_{Par2}^{\pm}(L) + \hat{T}_{Par3}^{\pm}(L))$$

$$T_{2,j}^{\pm} = \frac{1}{7}\sum_{L=L_j^{min}}^{L_j^{max}}\hat{T}_{Par4}^{\pm}(L)$$

$$T_{3,j}^{\pm} = \frac{1}{7}\sum_{L=L_j^{min}}^{L_j^{max}}\frac{1}{3}(\hat{T}_{Par5}^{\pm}(L) + \hat{T}_{Par6}^{\pm}(L) + \hat{T}_{Par7}^{\pm}(L))$$

$$T_{4,j}^{\pm} = \frac{1}{7}\sum_{L=L_j^{min}}^{L_j^{max}}\hat{T}_{Par8}^{\pm}(L)$$

In this example, the different contributions of the primary parameters in the individual groups are weighted equally, the first parameter group includes e.g. three rhythmological variables (called Par1 through Par3 here), the second includes an activity variable (Par4), the third includes three intracardial impedance variables (Par5 through Par7), and the fourth includes an intrathoracic impedance variable (Par8). The values of the $\alpha_{k,j}^{\pm}$ were optimized as described earlier in the foregoing after discrete values were provided in the training process.

Figure 3A:
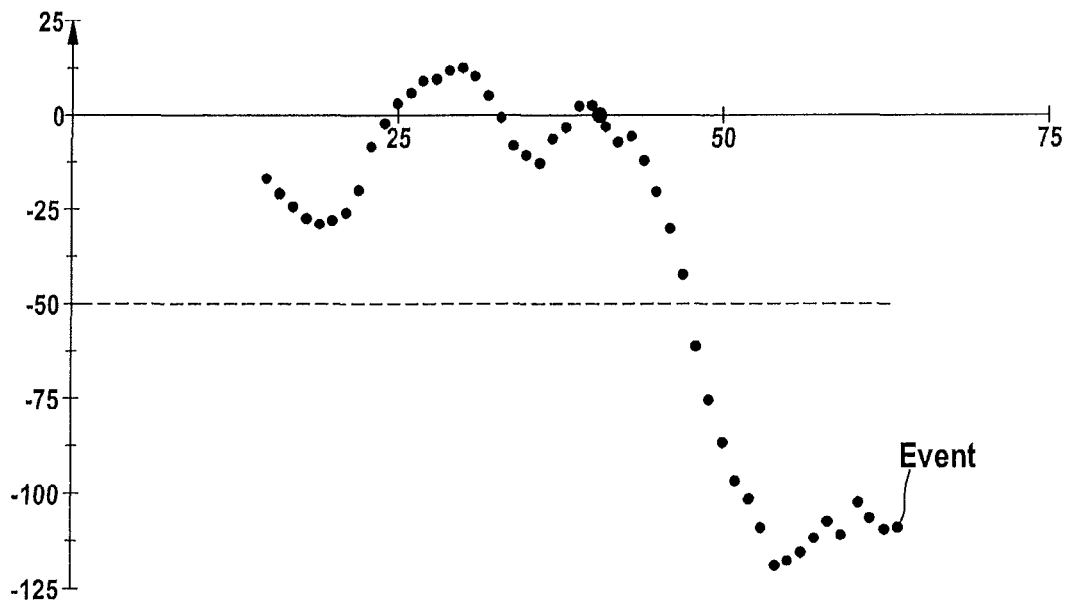
FIG. 3A is a first example of a predictor progression over time.
Figure 3B:
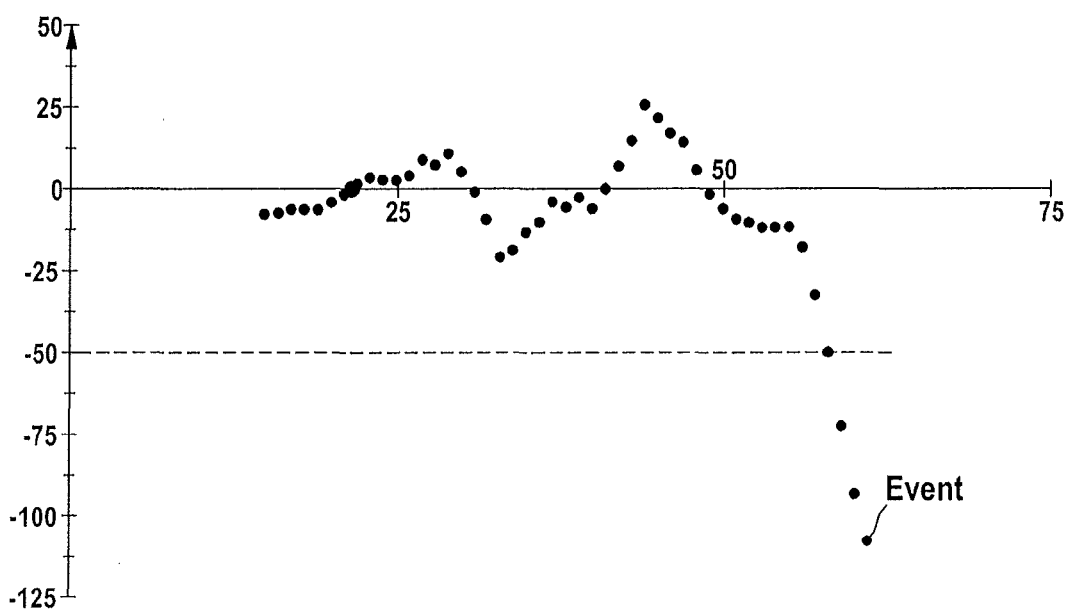
FIG. 3B is a second example of a predictor progression over time.

FIGS. 3A and 3B provide an exemplary graphic depiction of the progression of specific predictor values for two patients in arbitrary units over time in days. A large circle indicates a day on which there was a follow-up, and the threshold is indicated with a broken line. In FIG. 3A the event was detected 16 days prior to occurrence; in FIG. 3B it was detected three days in advance. In each case, the physician would have been able to intervene in advance given a suitable alarm system, which may provide notice to the physician of the predicted event.

The invention is not limited in its embodiment to the preferred exemplary embodiments described in the foregoing. On the contrary, a number of variants are possible that have fundamentally different types of embodiments but make use of the inventive arrangement, the inventive method, the inventive computer program, and/or the inventive corresponding computer-readable storage medium.

We claim:

1. A method for predicting at least one system event comprising:

determining, by at least one sensor, values $s_j$ of at least one primary parameter $S_j$ within at least one time window having the length L, determining, by at least one data processing device connected to the at least one sensor, a frequency $\tau$ of a trend for at least a portion of the at least one primary parameter $S_j$ for at least a part of the time window, and signaling, by the at least one data processing device, an occurrence of a system event based on the frequency τ of a trend or initiating at least one system event-related measure to address the system event, wherein the frequency τ of a trend for the at least one time window of the length L, $L_{min} \leq L \leq L_{max}$, and for a time of prediction H, $H_{min} \leq H \leq H_{max}$ is determined, wherein the window length L and the time of prediction H are different length time periods occurring before the system event, wherein the at least one time window is comprised of a plurality of time windows, groups of primary parameters $S_j$ are formed, and an average $\hat{T}_i^\pm$ for at least one of frequency τ and frequency $\tau_i$ for the time windows are found for at least one group q of primary parameters, wherein features $T_k^\pm$ formed from the primary parameters are combined in the at least one group q according to $$T_k^\pm = \frac{\frac{1}{n_i^q}\sum_{j=1}^{n_i^q} \beta_j \hat{T}_j^\pm(S_j)}{\sum_{j=1}^{n_i^q} \beta_j}, k = 1, \ldots, N^q,$$

wherein $N_q$ is the number of groups, each group q combining a number of $n_i^q$ measured variables (where i=1, ..., $N^q$), and the group q comprising only one $\hat{T}_i^\pm$, and the measured variables determined, weighted by relevance, using weighting factors $\beta_j$, wherein $T_k^+$ and $T_k^-$, which belong to a same group, are included in a classification method as combined variable $T_k^\pm$, and wherein the classification method provides an indicator to suggest the occurrence of the system event.

2. The method of claim 1, wherein the at least one time window is divided into a plurality of intervals and the frequency $\tau_i$ of the trend within the intervals is determined for at least one primary parameter $S_j$.

3. The method of claim 2, wherein the at least one time window is comprised of a plurality of time windows that are divided into intervals as a function of a primary parameter $S_j$.

4. The method of claim 2, wherein an average for at least one of frequency τ and frequency $\tau_i$ are found for a number of time windows.

5. The method of claim 1, wherein determining the trend comprises testing a hypothesis for a presence of the trend.

6. The method of claim 1, wherein the trend is an increasing or decreasing trend.

7. The method of claim 1, further comprising downloading from an electronic data network to a data processing device connected to the data network a computer program configured to have the data processing device perform the determining values $s_j$ of at least one primary parameter $S_j$ within at least one time window having the length L, the determining a frequency τ of a trend for at least a portion of the at least one primary parameter $S_j$ for at least a part of the time window, and the signaling an occurrence of a system event based on the frequency τ of a trend or initiating a system event-related measures to address the system event.

8. An arrangement having at least one chip and/or processor, the arrangement being configured to predict at least one system event by:

determining, by at least one sensor, values $s_j$ of at least one primary parameter $S_j$ within at least one time window having the length L, determining, by at least one data processing device connected to the at least one sensor, a frequency τ of a trend for at least a portion of the at least one primary parameter $S_j$ for at least a part of the time window, and signaling, by the at least one data processing device, an occurrence of a system event based on the frequency τ of a trend and initiating at least one system event-related measure to address the system event, wherein the frequency τ of a trend for the at least one time window of the length L, $L_{min} \leq L \leq L_{max}$, and for a time of prediction H, $H_{min} \leq H \leq H_{max}$ is determined, wherein the window length L and the time of prediction H are different length time periods occurring before the system event, wherein the at least one time window is comprised of a plurality of time windows, groups of primary parameters $S_j$ are formed, and an average $\hat{T}_i^\pm$ for at least one of frequency τ and frequency $\tau_i$ for the time windows are found for at least one group q of primary parameters, wherein features $T_k^\pm$ formed from the primary parameters are combined in the at least one group q according to $$T_k^\pm = \frac{\frac{1}{n_i^q}\sum_{j=1}^{n_i^q} \beta_j \hat{T}_j^\pm(S_j)}{\sum_{j=1}^{n_i^q} \beta_j}, k = 1, \ldots, N^q,$$

wherein $N^q$ is the number of groups, each group q combining a number of $n_i^q$ measured variables (where i=1, ..., $N^q$), and the group q comprising only one $\hat{T}_i^\pm$, and the measured variables determined, weighted by relevance, using weighting factors $\beta_j$, wherein $T_k^+$ and $T_k^-$, which belong to a same group, are included in a classification method as combined variable $T_k^\pm$, and wherein the classification method provides an indicator to suggest the occurrence of the system event.

9. The arrangement in accordance with claim 8, wherein the at least one sensor is comprised of probes and/or sensors for system-internal and/or system-external acquisition of measured values $s_j$ for at least one primary parameter $S_j$.

10. The arrangement of claim 8, wherein the at least one sensor comprises an active or passive implant for measuring the measured values $s_j$.

11. The arrangement of claim 8, wherein the arrangement is configured such that at least some obtained measured values $s_j$ are evaluated in an implant and/or in a data processing device that is arranged remote from the implant.

12. A data processing device having a computer program stored in memory of the data processing device wherein the computer program is configured to execute a method for predicting at least one system event, the method comprising:

determining, by at least one sensor, values $s_j$ of at least one primary parameter $S_j$ within at least one time window having the length L, determining, by at least one data processing device connected to the at least one sensor, a frequency τ of a trend for at least a portion of the at least one primary parameter $S_j$ for at least a part of the time window, and signaling, by the at least one data processing device, an occurrence of a system event based on the frequency τ of a trend or initiating at least one system event-related measure to address the system event, wherein the frequency τ of a trend for the at least one time window of the length L, $L_{min} \leq L \leq L_{max}$, and for a time of prediction H, $H_{min} \leq H \leq H_{max}$ is determined, wherein the window length L and the time of prediction H are different length time periods occurring before the system event, wherein the at least one time window is comprised of a plurality of time windows, groups of primary parameters $S_j$ are formed, and an average $\hat{T}_i^{\pm}$ for at least one of frequency τ and frequency $\tau_i$ for the time windows are found for at least one group q of primary parameters, wherein features $T_k^{\pm}$ formed from the primary parameters are combined in the at least one group q according to $$T_k^{\pm} = \frac{\frac{1}{n_i^q}\sum_{j=1}^{n_i^q} \beta_j \hat{T}_j^{\pm}(S_j)}{\sum_{j=1}^{n_i^q} \beta_j}, k = 1, \ldots, N^q,$$

wherein $N^q$ is the number of groups, each group q combining a number of $n_i^q$ measured variables (where $i=1, \ldots, N_q$), and the group q comprising only one $\hat{T}_i^{\pm}$ and the measured variables determined, weighted by relevance, using weighting factors $\beta_j$, wherein $T_k^+$ and $T_k^-$, which belong to a same group, are included in a classification method as combined variable $T_k^+$, and wherein the classification method provides an indicator to suggest the occurrence of the system event.

13. A non-transitory computer-readable storage medium on which a program is stored, the program configured such that a data processing device is able to execute a method for predicting at least one system event after the data processing device has the program loaded into memory of the data processing device, the method comprising:

determining, by at least one sensor, values $s_j$ of at least one primary parameter $S_j$ within at least one time window having the length L, determining, by at least one data processing device connected to the at least one sensor, a frequency τ of a trend for at least a portion of the at least one primary parameter $S_j$ for at least a part of the time window, and signaling, by the at least one data processing device, an occurrence of a system event based on the frequency τ of a trend or initiating at least one system event-related measure to address the system event, wherein the frequency τ of a trend for the at least one time window of the length L, $L_{min} \leq L \leq L_{max}$, and for a time of prediction H, $H_{min} \leq H \leq H_{max}$ is determined, and wherein the window length L and the time of prediction H are different length time periods occurring before the system event, wherein the at least one time window is comprised of a plurality of time windows, groups of primary parameters $S_j$ are formed, and an average $\hat{T}_i^{\pm}$ for at least one of frequency τ and frequency $\tau_i$ for the time windows are found for at least one group q of primary parameters, wherein features $T_k^{\pm}$ formed from the primary parameters are combined in the at least one group q according to $$T_k^{\pm} = \frac{\frac{1}{n_i^q}\sum_{j=1}^{n_i^q} \beta_j \hat{T}_j^{\pm}(S_j)}{\sum_{j=1}^{n_i^q} \beta_j}, k = 1, \ldots, N^q,$$

wherein $N^q$ is the number of groups, each group q combining a number of $n_i^q$ measured variables (where $i=1, \ldots, N^q$), and the group q comprising only one $\hat{T}_i^{\pm}$, and the measured variables determined, weighted by relevance, using weighting factors $\beta_j$, wherein $T_k^+$ and $T_k^-$, which belong to a same group, are included in a classification method as combined variable $T_k^+$, and wherein the classification method provides an indicator to suggest the occurrence of the system event.

14. A method for determining a system event comprising:

measuring at least one variable with at least one sensor, each variable being a variable of a physiological system or a technical system;

at least one data processing device connected to the at least one sensor determining values $s_j$ of at least one primary parameter $S_j$ within at least one time window having the length L based on the measured at least one variable, the at least one data processing device determining a frequency τ of a trend for at least a portion of the at least one primary parameter $S_j$ for at least a part of the time window, and the at least one data processing device signaling an occurrence of a system event based on the frequency τ of a trend or initiating at least one system event-related measure to address the system event, wherein the frequency τ of a trend for the at least one time window of the length L, $L_{min} \leq L \leq L_{max}$, and for a time of prediction H, $H_{min} \leq H \leq H_{max}$ is determined, and wherein the window length L and the time of prediction H are different length time periods occurring before the system event, wherein the at least one time window is comprised of a plurality of time windows, groups of primary parameters $S_j$ are formed, and an average $\hat{T}_i^{\pm}$ for at least one of frequency τ and frequency $\tau_i$ for the time windows are found for at least one group q of primary parameters, wherein features $T_k^{\pm}$ formed from the primary parameters are combined in the at least one group q according to $$T_k^{\pm} = \frac{\frac{1}{n_i^q}\sum_{j=1}^{n_i^q} \beta_j \hat{T}_j^{\pm}(S_j)}{\sum_{j=1}^{n_i^q} \beta_j}, k = 1, \ldots, N^q,$$

wherein $N^q$ is the number of groups, each group q combining a number of $n_i^q$ measured variables (where $i=1, \ldots, N^q$), and the group q comprising only one $\hat{T}_i^{\pm}$, and the measured variables determined, weighted by relevance, using weighting factors $\beta_j$, wherein $T_k^+$ and $T_k^-$, which belong to a same group, are included in a classification method as combined variable $T_k^+$, and wherein the classification method provides an indicator to suggest the occurrence of the system event.

15. The method of claim 14, wherein the signaling is an output for an alarm.

16. The method of claim 14, wherein the at least one data processing device is remote from the at least one sensor and is wirelessly connected to the at least one sensor.

17. The method of claim 14, wherein the system event is a predicted event of a physiological system, a network system, an economic system, a business system, a pathophysiological system, or a geological system.

18. The method of claim 14, wherein the at least one sensor is comprised of a plurality of sensors, the sensors being configured to obtain intracardial electrogram data for determining impedances and pressure and wherein the at least one data processing device is comprised of an analysis unit.

\* \* \* \* \*